United States Patent [19]

Beli et al.

[11] Patent Number: 5,071,772

[45] Date of Patent: Dec. 10, 1991

[54] DEVICE FOR CARRYING OUT EXTEMPORANEOUS QUANTITATIVE DIAGNOSTIC TESTS ON WHOLE BLOOD

[76] Inventors: Raffaele Beli, Via Lupia, 5, Lecce; Arturo Corchia, Via delle Lenze, 3, Pisa, both of Italy

[21] Appl. No.: 307,253

[22] Filed: Feb. 7, 1989

[51] Int. Cl.$^5$ ............................................. G01N 31/22
[52] U.S. Cl. ...................................... 422/56; 422/58; 435/805
[58] Field of Search ................. 436/169, 170; 435/805; 422/56, 57

[56] References Cited

U.S. PATENT DOCUMENTS

| | | | |
|---|---|---|---|
| 3,881,993 | 5/1975 | Freake et al. | 435/30 |
| 4,040,787 | 8/1977 | Roy et al. | 436/108 |
| 4,160,008 | 7/1979 | Fencketti et al. | 422/56 |
| 4,212,938 | 7/1980 | Gruber et al. | 435/11 |
| 4,234,313 | 11/1980 | Faulkner | 436/99 |
| 4,301,115 | 11/1981 | Ropkin et al. | 422/57 |
| 4,349,208 | 9/1982 | Long | 436/99 |
| 4,529,708 | 7/1985 | Stephens | 436/98 |
| 4,592,893 | 6/1986 | Poppe et al. | 422/56 |
| 4,797,256 | 1/1989 | Watlington, IV | 422/58 |
| 4,837,373 | 6/1989 | Gunkel et al. | 436/169 |
| 4,883,764 | 11/1989 | Kloepfer | 422/57 |

OTHER PUBLICATIONS

Windholz et al., *The Merck Index,* 1983, pp. 812, #5509.
Hawley, *The Condensed Chemical Dictionary,* 1981, p. 637.
Grant, *Hackh's Chemical Dictionary,* 1969, p. 301.
Windholz et al. *The Merck Index,* 1983, p. 1221, #8331.

*Primary Examiner*—Robert J. Warden
*Assistant Examiner*—Theresa A. Trembley
*Attorney, Agent, or Firm*—Birch, Stewart, Kolasch & Birch

[57] ABSTRACT

A device for carrying out extemporaneous quantitive diagnostic tests on the whole blood which comprises:
a rigid plastic strip, to the end of which there is cemented a substrate containing a reactive substance which undergoes a selective color reaction respectively with the substance to be determined in the blood, and
a visual colorimetric reference scale specific for each of the examined substances and possibly corrected so as to directly read the content of the examined substance in the plasma from the test carried out the whole blood.

5 Claims, No Drawings

DEVICE FOR CARRYING OUT EXTEMPORANEOUS QUANTITATIVE DIAGNOSTIC TESTS ON WHOLE BLOOD

FIELD OF THE INVENTION

This invention relates to a device and the relative method for carrying out extemporaneous quantitative diagnostic tests on whole blood.

More particularly, the invention relates to a device and a method based on color reactions for the extemporaneous determination of uricemia, azotemia, creatininemia and cholesterolemia in the whole blood.

The device and method of the present invention are of considerable use in checking patients who, after initial scrupulous control of their illness, tend to lose this control as they are unwilling to periodically attend the analysis laboratory because of the bureaucracy involved and the risk of losing their entire work day.

In this respect the tests according to the invention can be carried out in the home by a simple manual procedure and require only a short time.

For the determination of uricemia, creatininemia, azotemia and cholesterolemia, the detection of uric acid, creatinine, urea and cholesterol, respectively, is used.

PRIOR ART

Elements in the form of tapes are known comprising a transparent support and a layer containing a reactive substance which changes color by reaction with one of the components of the liquid under examination, such as the blood, the quantitative determination being done spectrophotometrically (G.B. patent 1,440,464). Strips are also known for diagnostic tests for determining blood and hemoglobin in biological materials, these comprising an unsized paper support impregnated with an organic hydroperoxide, a buffer acid, a chromogen, a wetting agent, a filmogenic polymer substance and an agent able to accelerate the activity of the peroxide.

The method is suitable for example for determining blood in the urine (G.B. patent 1,490,380).

The various known methods do not however satisfy the requirement for the extemporaneous determination in the home of uricemia, azotemia, creatininemia and cholesterolemia. The great importance of tests relating to these hematic indices is illustrated by the following considerations.

The uric acid content in the blood is an index of purine metabolism and of renal functionality; the creatininemia is the most reliable hematochemical index of renal insufficiency; the azotemia is an index of renal functionality but can be influenced by alterations in the circulation of both general and local kind (hypotension, shock, dehydration, vomit and diarrhea), by diet, by illnesses accompanied by relevant tissue destruction and by the use of certain drugs (cortisones, tetracyclines); the cholesterolemia increases in essential hypercholesterolemia, in mixed hyperlipemias, in secondary hyperlipemias (nephrotic syndrome, myxedemia, diabetes melitus, biliary cirrhosis, obstructive jaundice) and in Cushing's disease.

Determination of blood cholesterol is very important as a "humoral indication" of possible atherogenic tendency.

SUMMARY OF THE INVENTION

The aim of the present invention is to provide a device comprising:
a) a rigid plastic strip, to the end of which there is cemented a substrate containing a reactive substance which undergoes a selective color reaction respectively with the substance to be determined in the blood; and
b) a visual colorimetric reference scale specific for each of the examined substances and possibly corrected so as to directly read the content of the examined substance in the plasma from the test carried out on the whole blood. A further object of the present invention is to provide a method for carrying out the test comprising the following stages:
1) a drop of blood is withdrawn from the finger tip,
2) the whole blood is poured onto the substrate supported by the plastic strip and containing the reactive substance, and after one minute is removed by dry cotton wool,
3) a visual reading is made by comparison with said colorimetric scale one minute after removing the blood.

DETAILED DESCRIPTION OF THE INVENTION

A substrate able to undergo a color reaction with the substance sought in the blood is cemented to the end of a plastics strip.

The reactive substances used for incorporation into the substrate are: phosphotungstic acid for determining the uricemia, 1:1 (parts by weight) picric acid with sodium bicarbonate for determining the creatininemia, diacetyl monoxime for determining the azotemia, and the Liebermann-Burchard reagent for determining the cholesterolemia.

The substrate containing the reactive substance is prepared by depositing on unsized paper a layer of the reactive substance mixed with an inert substance able to give an homogeneous mixture of a pasty consistency, such as glycerol, PVC, gelatine and carboxymethylcellulose. Preferably a stabilizing substance, such as magnesium trisilicate, is also added.

In a preferred embodiment of the invention one part by weight of the reactive substance is mixed with one part by weight of magnesium trisilicate in form of a saturated solution and with two parts by weight of glycerol. The paste obtained is applied to the unsized paper to a thickness of 1–2 mm and is kept in a dry dark environment for 4–8 hours.

The substrate prepared in this manner is then cut preferably into small rectangles of 20–50 mm$^2$ each and each of these rectangles is glued by means of silicone or another inert glue onto a rigid plastic strip.

We have surprisingly found that when the substrate prepared as described comes into contact with the whole blood, it allows the substance under examination to react with the reactive substance while at the same time preventing interference with the chromogenic agents of the blood.

The procedure used in preparing said substrate can be carried out either manually or by industrial processes.

Separately, colorimetric scales are constructed on the basis of the color reactions of the substances incorporated in said substrates, for progressively increasing concentrations of the examined substances in the whole blood. It is advisable to repeat the colorimetric scale calibration for each stock of substrates, whether to be worked manually or industrially.

The colorimetric scale calibration is done by two methods, each having a different objective, namely either by introducing suitable correction factors by means of which the content of the examined substance in the plasma is read off directly even though the test is made on the whole blood, or without any correction in which case the result represents the total concentration of the examined substance in the whole blood. The correction factor derives from the difference between the content of the examined substance in whole blood and its content in plasma.

For example, considering that the uric acid in plasma represents 72.8% of that contained in whole blood, the value obtained by the test when carried out on the whole blood has to be reduced by 27.2%.

For the creatininemia the value obtained for the whole blood has to be reduced by 1.2%, whereas for the azotemia the reduction is 57.0%.

Obviously, if the figure of interest is that relative to the whole blood, such as when determining total cholesterolemia, no correction is made to the colorimetric scale.

The method for carrying out the tests according to the invention comprises the following stages:

1) a drop of blood is withdrawn from the finger tip,
2) the whole blood is poured onto the substrate supported by the plastic strip and containing the reactive substance, and after one minute is removed by dry cotton wool,
3) a visual reading is made by comparison with said colorimetric scale one minute after removing the blood. The reaction of the blood on said substrate containing the reactive substance is conducted at a temperature of between 18° and 30° C.

The tests for uricemia, creatininemia, azotemia and cholesterolemia conducted in accordance with the invention have all been checked by comparison with determinations made in the laboratory by the autoanalyzer system on 50 blood samples from patients having both normal and altered indices, the results being as follows.

In the uricemia determination test, 90% of the cases gave values which were perfectly superimposable on those determined by the autoanalyzer system whereas in the remaining 10% of cases the values showed a difference of not more than 20%.

In the creatininemia determination test, 93% of the cases gave values which were perfectly superimposable on those determined by the autoanalyzer system whereas in the remaining 7% of cases the values showed a difference of not more than 20%.

In the azotemia determination test the values obtained were all practically superimposable on those obtained by the autoanalyzer system.

In the total cholesterolemia determination test the results were completely superimposable on those obtained by autoanalyzer system.

We claim:

1. A device for carrying out extemporaneous quantitative diagnostic tests on whole blood by means of colorimetric determination of uricemia, creatininemia, azotemia, and cholesterolemia as single tests, said device comprising:
   (a) a rigid plastic strip, to the end of which there is cemented, by means of an inert glue, a substrate containing an inert substance, magnesium trisilicate as a stabilizing substance and a reactive substance which undergoes a selective color reaction, said reactive substance being selected from the group consisting of phosphotungstic acid, 1:1 parts by weight picric acid and sodium bicarbonate, diacetyl monoxime and the Liebermann-Buchard reagent; and
   (b) a visual colorimetric reference scale specific for each of the examined substances.

2. A device as claimed in claim 1, wherein said substrate is paper.

3. A device as claimed in claim 1, wherein said inert glue is silicone.

4. A device as claimed in claim 1, wherein said inert substance is selected from the group consisting of glycerol, PVC, gelatine and carboxymethylcellulose.

5. A device for carrying out extemporaneous quantitative diagnostic tests on whole blood by means of colorimetric determination of uricemia, creatininemia, azotemia, and cholesterolemia as single tests, said device comprising:
   (a) a rigid plastic strip, to the end of which there is cemented, by means of a silicone glue, a paper substrate containing an inert substance selected from the group consisting of glycerol, PVC, gelatine and carboxymethylcellulose, magnesium trisilicate as stabilizing substance and a reactive substance which undergoes a selective color reaction, said reactive substance being selected from the group consisting of phosphotungstic acid, 1:1 parts by weight picric acid and sodium bicarbonate, diacetyl monoxime and the Liebermann-Buchard reagent; and
   (b) a visual colorimetric reference scale specific for each of the examined substances.

* * * * *